United States Patent
Lee et al.

(10) Patent No.: US 8,782,681 B2
(45) Date of Patent: Jul. 15, 2014

(54) METHOD AND SYSTEM FOR RATING MEDIA AND EVENTS IN MEDIA BASED ON PHYSIOLOGICAL DATA

(75) Inventors: Hans C. Lee, Carmel, CA (US); Timmie T. Hong, San Diego, CA (US); William H. Williams, Hilo, HI (US); Michael R. Fettiplace, Madison, WI (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 946 days.

(21) Appl. No.: 11/804,555

(22) Filed: May 17, 2007

(65) Prior Publication Data

US 2008/0222671 A1     Sep. 11, 2008

Related U.S. Application Data

(60) Provisional application No. 60/905,616, filed on Mar. 8, 2007.

(51) Int. Cl.
    *H04H 60/33*     (2008.01)

(52) U.S. Cl.
    USPC ............................................... 725/10; 725/12

(58) Field of Classification Search
    USPC .......................... 434/236–238; 705/2–10, 12
    See application file for complete search history.

(56) References Cited

U.S. PATENT DOCUMENTS

| | | | |
|---|---|---|---|
| 4,695,879 A | * | 9/1987 | Weinblatt ........................ 725/10 |
| 4,755,045 A | | 7/1988 | Borah et al. |
| 4,846,190 A | | 7/1989 | John |
| 4,931,934 A | * | 6/1990 | Snyder ........................ 434/236 |
| 4,974,602 A | | 12/1990 | Abraham-Fuchs et al. |
| 5,024,235 A | | 6/1991 | Ayers |
| 5,243,517 A | | 9/1993 | Schmidt et al. |
| 5,405,957 A | | 4/1995 | Tang et al. |
| 5,447,166 A | | 9/1995 | Gevins |
| 5,450,855 A | | 9/1995 | Rosenfeld |
| 5,513,649 A | | 5/1996 | Gevins et al. |
| 5,579,774 A | | 12/1996 | Miller et al. |

(Continued)

FOREIGN PATENT DOCUMENTS

| | | |
|---|---|---|
| EP | 1052582 | 11/2000 |
| EP | 1389012 | 2/2004 |

(Continued)

OTHER PUBLICATIONS

Form PCT/ISA/220, PCT/US07/15019, "PCT Notification of Transmittal of The International Search Report and the Written Opinion of the International Searching Authority, or the Declaration," 1 pg. Jun. 11, 2008.

(Continued)

*Primary Examiner* — Brian T Pendleton
*Assistant Examiner* — Dika C. Okeke
(74) *Attorney, Agent, or Firm* — Hanley, Flight and Zimmerman, LLC

(57) ABSTRACT

Various embodiments of the present invention enable a bottom up analysis approach that derives physiological responses from measured physiological data of viewers of a media, and calculates scores of instances of an event type based on the physiological responses. The scores are then aggregated to rate the event type in addition to scoring the individual event instances. The approach can also form an overall rating of the media by aggregating the event ratings of set of event types within the media.

3 Claims, 7 Drawing Sheets

(56) References Cited

U.S. PATENT DOCUMENTS

| | | |
|---|---|---|
| 5,601,090 A | 2/1997 | Musha |
| 5,649,061 A | 7/1997 | Smyth |
| 5,676,138 A * | 10/1997 | Zawilinski ............... 600/301 |
| 5,692,906 A | 12/1997 | Corder |
| 5,724,987 A | 3/1998 | Gevins et al. |
| 5,740,812 A | 4/1998 | Cowan |
| 5,774,591 A * | 6/1998 | Black et al. ............... 382/118 |
| 5,983,129 A | 11/1999 | Cowan et al. |
| 5,983,214 A | 11/1999 | Lang et al. |
| 6,001,065 A | 12/1999 | DeVito |
| 6,099,319 A | 8/2000 | Zaltman et al. |
| 6,254,536 B1 | 7/2001 | DeVito |
| 6,259,889 B1 | 7/2001 | LeDue |
| 6,292,688 B1 * | 9/2001 | Patton ............... 600/544 |
| 6,309,342 B1 | 10/2001 | Blazey et al. |
| 6,322,368 B1 | 11/2001 | Young et al. |
| 6,349,231 B1 | 2/2002 | Musha |
| 6,425,764 B1 | 7/2002 | Lamson |
| 6,434,419 B1 | 8/2002 | Gevins et al. |
| 6,481,013 B1 | 11/2002 | Dinwiddie et al. |
| 6,585,521 B1 * | 7/2003 | Obrador ............... 725/12 |
| 6,606,102 B1 * | 8/2003 | Odom ............... 715/745 |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,656,116 B2 | 12/2003 | Kim et al. |
| 6,678,866 B1 | 1/2004 | Sugimoto et al. |
| 6,699,188 B2 | 3/2004 | Wessel |
| 6,792,304 B1 | 9/2004 | Silberstein |
| 6,839,682 B1 | 1/2005 | Blume et al. |
| 6,978,115 B2 | 12/2005 | Whitehurst et al. |
| 7,035,685 B2 | 4/2006 | Ryu et al. |
| 7,050,753 B2 | 5/2006 | Knutson |
| 7,113,916 B1 * | 9/2006 | Hill ............... 705/10 |
| 7,127,283 B2 | 10/2006 | Kageyama |
| 7,194,186 B1 | 3/2007 | Strub et al. |
| D565,735 S | 4/2008 | Washbon |
| 7,383,728 B2 | 6/2008 | Noble et al. |
| 7,627,880 B2 | 12/2009 | Itakura |
| 7,689,272 B2 | 3/2010 | Farwell |
| 7,716,697 B2 | 5/2010 | Morikawa et al. |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,853,122 B2 | 12/2010 | Miura et al. |
| 7,942,816 B2 | 5/2011 | Satoh et al. |
| 2001/0016874 A1 | 8/2001 | Ono et al. |
| 2001/0056225 A1 | 12/2001 | DeVito |
| 2002/0107454 A1 | 8/2002 | Collura et al. |
| 2002/0154833 A1 | 10/2002 | Koch et al. |
| 2002/0182574 A1 | 12/2002 | Freer |
| 2002/0188216 A1 | 12/2002 | Kayyali et al. |
| 2003/0003433 A1 | 1/2003 | Carpenter et al. |
| 2003/0055355 A1 | 3/2003 | Vieritio-Oja |
| 2003/0063780 A1 | 4/2003 | Gutta et al. |
| 2003/0066071 A1 | 4/2003 | Gutta et al. |
| 2003/0067486 A1 * | 4/2003 | Lee et al. ............... 345/751 |
| 2003/0076369 A1 | 4/2003 | Resner |
| 2003/0081834 A1 * | 5/2003 | Philomin et al. ............... 725/10 |
| 2003/0093784 A1 * | 5/2003 | Dimitrova et al. ............... 725/9 |
| 2003/0126593 A1 * | 7/2003 | Mault ............... 725/10 |
| 2003/0153841 A1 | 8/2003 | Kilborn |
| 2004/0013398 A1 | 1/2004 | Miura et al. |
| 2004/0018476 A1 | 1/2004 | LaDue |
| 2004/0039268 A1 | 2/2004 | Barbour et al. |
| 2004/0072133 A1 | 4/2004 | Kullok et al. |
| 2004/0077934 A1 | 4/2004 | Massad |
| 2004/0088289 A1 * | 5/2004 | Xu et al. ............... 707/3 |
| 2004/0111033 A1 | 6/2004 | Oung et al. |
| 2004/0161730 A1 | 8/2004 | Urman |
| 2004/0193068 A1 | 9/2004 | Burton et al. |
| 2004/0208496 A1 | 10/2004 | Pilu |
| 2004/0267141 A1 | 12/2004 | Amano et al. |
| 2005/0010087 A1 | 1/2005 | Banet |
| 2005/0010116 A1 | 1/2005 | Korhonen et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 * | 3/2005 | Martins ............... 725/10 |
| 2005/0096311 A1 | 5/2005 | Suffin et al. |
| 2005/0097594 A1 * | 5/2005 | O'Donnell et al. ............... 725/15 |
| 2005/0113656 A1 | 5/2005 | Chance |
| 2005/0120372 A1 | 6/2005 | Itakura |
| 2005/0143629 A1 | 6/2005 | Farwell |
| 2005/0165285 A1 | 7/2005 | Iliff |
| 2005/0172311 A1 | 8/2005 | Hjelt et al. |
| 2005/0223237 A1 * | 10/2005 | Barletta et al. ............... 725/9 |
| 2005/0289582 A1 * | 12/2005 | Tavares et al. ............... 725/10 |
| 2006/0010470 A1 * | 1/2006 | Kurosaki et al. ............... 725/46 |
| 2006/0064037 A1 | 3/2006 | Shalon et al. |
| 2006/0094970 A1 | 5/2006 | Drew |
| 2006/0111621 A1 | 5/2006 | Coppi et al. |
| 2006/0143647 A1 | 6/2006 | Bill |
| 2006/0217598 A1 | 9/2006 | Miyajima et al. |
| 2006/0258926 A1 | 11/2006 | Ali et al. |
| 2006/0265022 A1 | 11/2006 | John et al. |
| 2006/0277102 A1 | 12/2006 | Agliozzo |
| 2006/0293608 A1 | 12/2006 | Rothman et al. |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1 | 3/2007 | Le et al. |
| 2007/0116037 A1 | 5/2007 | Moore |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0265507 A1 | 11/2007 | De Lemos |
| 2008/0039737 A1 | 2/2008 | Breiter et al. |
| 2008/0091512 A1 * | 4/2008 | Marci et al. ............... 705/10 |
| 2008/0144882 A1 | 6/2008 | Leinbach et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0201731 A1 * | 8/2008 | Howcroft ............... 725/13 |
| 2008/0211768 A1 | 9/2008 | Breen et al. |
| 2008/0218472 A1 | 9/2008 | Breen et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0082643 A1 | 3/2009 | Pradeep et al. |
| 2009/0083129 A1 | 3/2009 | Pradeep et al. |
| 2009/0105576 A1 | 4/2009 | Do et al. |
| 2009/0112077 A1 | 4/2009 | Nguyen et al. |
| 2009/0156925 A1 | 6/2009 | Jin et al. |
| 2009/0214060 A1 | 8/2009 | Chuang et al. |

(56) References Cited

U.S. PATENT DOCUMENTS

2009/0222330 A1 9/2009 Leinbach
2010/0076333 A9 3/2010 Burton et al.

FOREIGN PATENT DOCUMENTS

| | | |
|---|---|---|
| EP | 1607842 | 12/2005 |
| JP | 05293172 | 11/1993 |
| JP | 07-329657 | 12/1995 |
| JP | 2002-000577 | 1/2002 |
| JP | 2002056500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003522580 | 7/2003 |
| JP | 2005084770 | 3/2006 |
| JP | 2006-323547 | 11/2006 |
| KR | 10-2000-0072489 | 12/2000 |
| KR | 10-2001-0104579 | 11/2001 |
| WO | 00/17824 | 3/2000 |
| WO | 01/97070 | 12/2001 |
| WO | 2004/100765 | 11/2004 |
| WO | 2006/005767 | 1/2006 |
| WO | 2007/019584 | 2/2007 |

OTHER PUBLICATIONS

Form PCT/ISA/210, PCT/US07/15019, "PCT International Search Report," 2 pgs. Jun. 11, 2008.
Form PCT/ISA/237, PCT/US07/15019, "PCT Written Opinion of the International Searching Authority," 5 pgs. Jun. 11, 2008.
Form PCT/IB/326, PCT/US07/015019, "Notification Concerning Transmittal of International Preliminary Report on Patentability," Sep. 17, 2009.
Form PCT/IB/373, PCT/US07/15019, "International Preliminary Report on Patentability." Sep. 8, 2009.
Form PCT/ISA/220, PCT/US07/14955, "PCT Notification of Transmittal of the International Search Report and the Written Opinion of the International Searching Authority, or the Declaration," 1 pg. Jul. 3, 2008.
Form PCT/ISA/210, PCT/US07/14955, "PCT International Search Report," 2 pgs. Jul. 3, 2008.
Form PCT/ISA/237, PCT/US07/14955, "PCT Written Opinion of the International Searching Authority," 6 pgs. Jul. 3, 2008.
Form PCT/IB/326, PCT/US07/14955, "Notification Concerning Transmittal of International Preliminary Report on Patentability." 1 page Sep. 17, 2009.
Form PCT/IB/373, PCT/US07/14955, "International Preliminary Report on Patentability,"1 page Sep. 8, 2009.
Form PCT/ISA/220, PCT/US07/16796, "PCT Notification of Transmittal of the International Search Report and the Written Opinion of the International Searching Authority, or the Declaration," 1 pg. Jul. 3, 2008.
Form PCT/ISA/210, PCT/US07/16796,"PCTInternational Search Report," 2 pgs. Jul. 3, 2008.
Form PCT/ISA/237, PCT/US07/16796, "PCT Written Opinion of the International Searching Authority," 6 pgs. Jul. 3, 2008.
Form PCT/IB/326, PCT/US07/16796, "Notification Concerning Transmittal of International Preliminary Report on Patentability." 1 page Sep. 17, 2009.
Form PCT/IB/373, PCT/US07/16796, "International Preliminary Report on Patentability," 1 page Sep. 8, 2009.
Form PCT/ISA/220, PCT/US06/31569, "PCT Notification of Transmittal the International Search Report and the Written Opinion of the International Searching Authority, or the Declaration," 1 pg. Feb. 20, 2007.
Form PCT/ISA/210, PCT/US06/31569, "PCT International Search Report," 3 pgs. Feb. 20, 2007.
Form PCT/ISA/237, PCT/US06/31569, "PCT Written Opinion of the International Searching Authority," 6 pgs. Feb. 20, 2007.

Form PCT/IB/326, PCT/US06/31569,"Notification Concerning Transmittal of International Preliminary Report on Patentability." 1 page Mar. 13, 2008.
Form PCT/IB/373, PCT/US06/31569, "International Preliminary Report on Patentability." 1 page Mar. 4, 2008.
Form PCT/ISA/220, PCT/US07/20714, "PCT Notification of Transmittal of the International Search Report and the Written Opinion of the International Searching Authority, or the Declaration," 1 pg. Apr. 8, 2008.
Form PCT/ISA/210, PCT/US07/20714, "PCT International Search Report," 2 pgs. Apr. 8, 2008.
Form PCT/ISA/237, PCT/US07/20714, "PCT Written Opinion of the International Searching Authority," 6 pgs. Apr. 8, 2008.
Form PCT/IB/326, PCT/US07/20714, "Notification Concerning Transmittal of International Preliminary Report on Patentability." 1 page Sep. 17, 2009.
Form PCT/IB/373, PCT/US07/20714, "International Preliminary Report on Patentability," 1 page Sep. 8, 2008.
Form PCT/ISA/220, PCT/US07/17764, "PCT Notification of Transmittal of the International Search Report and the Written Opinion of the International Searching Authority, or the Declaration," 1 pg. May 6, 2008.
Form PCT/ISA/210, PCT/US07/17764, "PCT International Search Report," 2 pgs. May 6, 2008.
Form PCT/ISA/237, PCT/US07/17764, "PCT Written Opinion of the International Searching Authority," 7 pgs. May 6, 2008.
Form PCT/IB/326, PCT/US07/17764, "Notification Concerning Transmittal of International Preliminary Report on Patentability," 1 page Sep. 17, 2009.
Form PCT/IB/373, PCT/US07/17764, "International Preliminary Report on Patentability," 1 page Sep. 8, 2008.
Form PCT/ISA/220, PCT/US07/20713, "PCT Notification of Transmittal of the International Search Report and the Written Opinion of the International Searching Authority, or the Declaration," 1 pg. May 13, 2008.
Form PCT/ISA/210, PCT/US07/20713, "PCT International Search Report," 2 pgs. May 13, 2008.
Form PCT/ISA/237, PCT/US07/20713, "PCT Written Opinion of the International Searching Authority," 5 pgs. May 13, 2008.
Form PCT/IB/326, PCT/US07/20713, "Notification Concerning Transmittal of International Preliminary Report on Patentability." 1 page Sep. 17, 2009.
Form PCT/IB/373, PCT/US07/20713, "International Preliminary Report on Patentability." 1 page Sep. 8, 2009.
Form PCT/ISA/220, PCT/US08/09110, "PCT Notification of Transmittal of The International Search Report and the Written Opinion of the International Searching Authority, or the Declaration," 1 pg, Feb. 20, 2009.
Form PCT/ISA/210, PCT/US08/09110, "PCT International Search Report," 3 pgs. Feb. 20, 2009.
Form PCT/ISA/237, PCT/US08/09110, "PCT Wrtten Opinion of the International Searching Authority," 4 pgs, Feb. 20, 2009.
Form PCT/ISA/220, PCT/US08/75640, "PCT Notification of Transmittal of The International Search Report and the Written Opinion of the International Searching Authority, or the Declaration," 1 pg. Nov. 7, 2008.
Form PCT/ISA/210, PCT/US08/75640, "PCT International Search Report," 2 pgs. Feb. 20, 2009.
Form PCT/ISA/237, PCT/US08/75640, "PCT Written Opinion of the International Searching Authority,"3 pgs. Feb. 20, 2009.
Form PCT/ISA/220, PCT/US08/78633, "PCT Notification of Transmittal of The International Search Report and the Written Opinion of the International Searching Authority, or the Declaration," 1 pg. Dec. 5, 2008.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs. Dec. 5, 2008.
Form PCT/ISA/220, PCT/US08/82147, "PCT Notification of Transmittal of The International Search Report and the Written Opinion of the International Searching Authority, or the Declaration," 1 pg. Jan. 21, 2009.
Form PCT/ISA/210, PCT/US08/82147, "PCT International Search Report," 2 pgs. Jan. 21, 2009.

(56) References Cited

OTHER PUBLICATIONS

Form PCT/ISA/237, PCT/US08/82147, "PCT Written Opinion of the International Searching Authority," 13 pgs. Jan. 21, 2009.
Form PCT/ISA/220, PCT/US08/82149, "PCT Notification of Transmittal of The International Search Report and the Written Opinion of the International Searching Authority, or the Declaration." 1 pg. Jan. 21, 2009.
Form PCT/ISA/210, PCT/US08/82149, "PCT International Search Report," 2 pgs. Jan. 21, 2009.
Form PCT/ISA/237, PCT/US08/82149, "PCT Written Opinion of the International Searching Authority," 14 pgs. Jan. 21, 2009.
Form PCT/ISA/220, PCT/US08/75651, "PCT Notification of Transmittal of the International Search Report and the Written Opinion of the International Searching Authority, or the Declaration," 1 pg. Nov. 28, 2008.
Form PCT/ISA/210, PCT/US08/75651, "PCT International Search Report," 2 pgs. Nov. 28, 2008.
Form PCT/ISA/237, PCT/US08/75651, "PCT Written Opinion of the International Searching Authority," 9 pgs. Nov. 28, 2008.
Form PCT/ISA/220, PCT/US08/85723, "PCT Notification of Transmittal of The International Search Report and the Written Opinion of the International Searching Authority, or the Declaration," 1 pg. Mar. 20, 2009.
Form PCT/ISA/210, PCT/US08/85723, "PCT International Search Report," 2 pgs. Mar. 20, 2009.
Form PCT/ISA/237, PCT/US08/85723, "PCT Written Opinion of the International Searching Authority," 7 pgs. Mar. 20, 2009.
Form PCT/ISA/220, PCT/US08/85203, "PCT Notification of Transmittal of The International Search Report and the Written Opinion of the International Searching Authority, or the Declaration," 1 pg, Feb. 27, 2009.
Form PCT/ISA/210, PCT/US08/85203, "PCT International Search Report," 2 pgs. Feb. 27, 2009.
Form PCT/ISA/237, PCT/US08/85203, "PCT Written Opinion of the International Searching Authority," 6 pgs. Feb. 27, 2009.
Form PCT/ISA/220, PCT/US08/75649, "PCT Notification of Transmittal of the International Search Report and the Written Opinion of the International Searching Authority, or the Declaration," 1 pg. Nov. 19, 2008.
Form PCT/ISA/210, PCT/US08/75649, "PCT International Search Report," 3 pgs, Nov. 19, 2008.
Form PCT/ISA/237, PCT/US08/75649, "PCT Written Opinion of the International Searching Authority," 5 pgs. Nov. 19, 2008.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalpgraphy Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Seldon, G (1981) "Machines that Read Minds." Science Digest, Oct. 1981.
Willis, M. & Hodson, V.; Discover Your Child's Learning Style: Children Learn in Unique Ways-Here's the Key to Ever Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry, Journal of Neuropsychiatry and Clinical Neurosciences. vol. 11(2): 190-208.
Decision of Rejection, English Language, issued by the State Intellectual Property Office of the P.R. China, in connection with Chinese application No. 201210063607.5, on Nov. 19, 2013, 10 pages.
Decision of Rejection, Chinese Language, issued by the State Intellectual Property Office of the P.R. China, in connection with Chinese application No. 201210063607.5, on Nov. 19, 2013, 6 pages.
Final Office Action, issued by the United States Patent and Trademark Office in connection with United States application No. 13/553,515 on Jan. 9, 2014, 13 pages.
European Office Action, issued by the European Patent Office in connection with European Patent Application 07 852 430.3, on Feb. 3, 2014, 3 pages.
First Office Action and Search Report, with English Language Version, issued by the State Intellectual Property Office of the Peoples' Republic of China, in connection with Chinese Patent Application No. 201210244954.8, on Jan. 2, 2014, 25 pages.
Interrogative Statement, English Language, issued by the Intellectual Property Office of Japan, in connection with Japanese application No. 2009-552656, on Oct. 25, 2013, 4 pages.
European Office Action, issued by the European Patent Office in connection with European Patent Application No. 07796518.4, on Sep. 13, 2013, 7 pages.
European Office Action, issued by the European Patent Office in connection with European Patent Application No. 07838838.6, on Oct. 23, 2013, 4 pages.
Office Action, issued by the United States Patent and Trademark Office in connection with U. S. Appl. No. 13/553,515 on Jul. 17, 2013, 12 pages.
Notice of Allowance and Fee(s) Due, issued by the United States Patent and Trademark Office in connection with U.S. Appl. No. 11/845,993, on Feb. 19, 2014, 10 pages.
Notice for Reasons for Rejection, English Language, issued by the Intellectual Property Office of Japan, in connection with Japanese application No. 2009-552661, on Apr. 24, 2013, 2 pages.
Decision of Rejection, English Language, issued by the State Intellectual Property Office of the P.R. China, in connection with Chinese application No. 200780052879.2, on May 29, 2013, 11 pages.
Decision of Rejection, Chinese Language, issued by the State Intellectual Property Office of the P.R. China, in connection with Chinese application No. 200780052879.2, on May 29, 2013, 7 pages.
Final Office Action, issued by the United States Patent and Trademark Office in connection with U.S. Appl. No. 11/835,634 on Jun. 20, 2013, 23 pages.
Notification of Reasons(s) for Rejection, issued by the Japanese Intellectual Property Office in connection with Japanese Patent Application No. 2012-152836, Jan. 14, 2014, 5 pages.
Notification of Grant of Patent Right for Invention, issued by the State Intellectual Property Office of the P.R. China, in connection with Chinese Patent Application No. 200780052869.9, on Aug. 31, 2012, 1 page.
Notification of the Third Office Action, issued by the State Intellectual Property Office of the P.R. China, in connection with Chinese Patent Application No. 200780052868.4, on Aug. 9, 2012, 7 pages.
Notification of the Second Office Action, issued by the State Intellectual Property Office of the P.R. China, in connection with Chinese Patent Application No. 200780052879.2, on May 4, 2012, 11 pages.
Notification of the Third Office Action, issued by the State Intellectual Property Office of the P.R. China, in connection with Chinese Patent Application No. 200680031159.3, on Mar. 28, 2012, 6 pages.

(56) References Cited

OTHER PUBLICATIONS

Notification of the Second Office Action, issued by the State Intellectual Property Office of the P.R. China, in connection with Chinese Patent Application No. 200680031159.3, on Oct. 19, 2011, 8 pages.
Notification of the Third Office Action, issued by the State Intellectual Property Office of the P.R. China, in connection with Chinese Patent Application No. 200780052879.2, on Dec. 31, 2012, 10 pages.
European Office Action, issued by the European Patent Office in connection with European Patent Application 07 838 838.6, on September 5, 2012, 5 pages.
Supplemental European Search Report, issued by the European Patent Office in connection with European Patent Application No. 07796518.4, on Jul. 11, 2012, 8 pages.
European Office Action, issued by the European Patent Office in connection with European Patent Application No. 07 810 808.1, on Dec. 1, 2011, 6 pages.
Supplemental European Search Report, issued by the European Patent Office in connection with European Patent Appliation No. 06824810.3, on Nov. 22, 2011, 14 pages.
European Office Action, issued by the European Patent Office in connection with European Patent Application No. 07 852 430.3, on Mar. 6, 2012, 5 pages.
European Office Action, issued by the European Patent Office in connection with European Patent Application No. 07 852 430.3, on Feb. 6, 2013, 5 pages.
Supplemental European Search Report, issued by the European Patent Office in connection with European Patent Application No. 07811241.4, on Feb. 14, 2012, 6 pages.
European Office Action, issued by the European Patent Office in connection with European Patent Application No. 07 838 838.6, on Sep. 23, 2011, 4 pages.
Supplemental European Search Report, issued by the European Patent Office in connection with European Patent Application No. 06824810.3, on Nov. 3, 2011, 13 pages.
Supplemental European Search Report, issued by the European Patent Office in connection with European Patent Application No. 07796518.4, on Jul. 30, 2012, 9 pages.
Notification of Reason(s) for Rejection, issued by the Japanese Intellectual Property Office in connection with Japanese Patent Application No. 2010-501190, on Oct. 2, 2012, 5 pages.
Notification of Reason(s) for Rejection, issued by the Japanese Intellectual Property Office in connection with Japanese Patent Application No. 2009-552658, on Apr. 19, 2012, 2 pages.
Notification of Reason(s) for Rejection, issued by the Japanese Intellectual Property Office in connection with Japanese Patent Application No. 2009-552657, on May 2, 2012, 5 pages.
Notification of Reason(s) for Rejection, issued by the Japanese Intellectual Property Office in connection with Japanese Patent Application No. 2009-552656, on Mar. 30, 2012, 3 pages.
Final Decision of Rejection, issued by the Japanese Intellectual Property Office in connection with Japanese Patent Application No. 2009-552656, on Jan. 21, 2013, 3 pages.
Notification of Reasons(s) for Rejection, issued by the Japanese Intellectual Property Office in connection with Japanese Patent Application No, 2008-529085, Nov. 29, 2011, 2 pages.
Notification of Reasons(s) for Rejection, issued by the Japanese Intellectual Property Office in connection with Japanese Patent Application No. 2009-552661, Nov. 13, 2012, 3 pages.
Notification of Reasons(s) for Rejection, issued by the Japanese Intellectual Property Office in connection with Japanese Patent Application No. 2009-552661, Apr. 24, 2013, 2 pages.
Notification of Reasons(s) for Rejection, issued by the Japanese Intellectual Property Office in connection with Japanese Patent Application No. 2009-552659, Nov. 16, 2012, 4 pages.
Notification of Reasons(s) for Rejection, issued by the Japanese Intellectual Property Office in connection with Japanese Patent Application No. 2009-552660, Nov. 16, 2012, 3 pages.
Notification of Reasons(s) for Rejection, issued by the Japanese Intellectual Property Office in connection with Japanese Patent Application No. 2009-552660, Mar. 13, 2013, 3 pages.
Notice of Allowance and Fee(s) Due, issued by the United States Patent and Trademark Office in connection with U.S. Appl. No. 11/804,517, on Mar. 21, 2012, 8 pages.
Final Rejection, issued by the United States Patent and Trademark Office in connection with U.S. Appl. No. 11/804,517, on Sep. 1, 2011, 11 pages.
Office Action, issued by the United States Patent and Trademark Office in connection with U.S. Appl. No. 11/804,517, on Feb. 3, 2011, 15 pages.
Final Rejection, issued by the United States Patent and Trademark Office in connection with U.S. Appl. No. 11/804,517, on Jun. 23, 2010, 14 pages.
Office Action, issued by the United States Patent and Trademark Office in connection with U.S. Appl. No. 11/804,517, on Sep. 17, 2009, 15 pages.
Office Action, issued by the United States Patent and Trademark Office in connection with U.S. Appl. No. 11/779,814, on Feb. 13, 2012, 19 pages.
Final Rejection, issued by the United States Patent and Trademark Office in connection with U.S. Appl. No. 11/779,814, on Jun. 28, 2012, 18 pages.
Final Rejection, issued by the United States Patent and Trademark Office in connection with U.S. Appl. No. 11/779,814, on Jun. 18, 2010, 24 pages.
Office Action, issued by the United States Patent and Trademark Office in connection with U.S. Appl. No. 11/779,814, on Oct. 5, 2009, 24 pages.
Final Rejection, issued by the United States Patent and Trademark Office in connection with U.S. Appl. No. 11/500,678, on Dec. 8, 2010, 9 pages.
Office Action, issued by the United States Patent and Trademark Office in connection with U.S. Appl. No. 11/500,678, on Mar. 17, 2010, 10 pages.
Office Action, issued by the United States Patent and Trademark Office in connection with U.S. Appl. No. 11/500,678, on Sep. 3, 2008, 12 pages.
Final Rejection, issued by the United States Patent and Trademark Office in connection with U.S. Appl. No. 11/500,678, on , Jun. 9, 2009, 11 pages.
Final Rejection, issued by the United States Patent and Trademark Office in connection with U.S. Appl. No. 11/845,993, on Apr. 24, 2012, 8 pages.
Advisory Action, issued by the United States Patent and Trademark Office in connection with U.S. Appl. No. 11/845,993, on Jul. 20, 2012, 4 pages.
Office Action, issued by the United States Patent and Trademark Office in connection with U.S. Appl. No. 11/845,993, Aug. 4, 2011, 12 pages.
Final Rejection, issued by the United States Patent and Trademark Office in connection with U.S. Appl. No. 11/835,634, on Apr. 25, 2012, 23 pages.
Office Action, issued by the United States Patent and Trademark Office in connection with U.S. Appl. No. 11/835,634, on Sep. 1, 2011, 16 pages.
Office Action, issued by the United States Patent and Trademark Office in connection with U.S. Appl. No. 11/835,634, on Feb. 26, 2013, 24, pages.
Final Rejection, issued by the United States Patent and Trademark Office in connection with U.S. Appl. No. 12/206,676, on Mar. 6, 2012, 9 pages.
Office Action, issued by the United States Patent and Trademark Office in connection with U.S. Appl. No. 12/206,676, on May 10, 2011, 9 pages.
Final Rejection, issued by the United States Patent and Trademark Office in connection with U.S. Appl. No. 12/206,702, on Jun. 3, 2010, 8 pages.
Office Action, issued by the United States Patent and Trademark Office in connection with U.S. Appl. No. 12/206,702, on May 28, 2009, 8 pages.
Final Rejection, issued by the United States Patent and Trademark Office in connection with U.S. Appl. No. 11/681,265, on Apr. 10, 2012, 18 pages.

(56) References Cited

OTHER PUBLICATIONS

Office Action, issued by the United States Patent and Trademark Office in connection with U.S. Appl. No. 11/681,265, on Jun. 21, 2011, 15 pages.
Restriction and/or Election Requirement, issued by the United States Patent and Trademark Office in connection with U.S. Appl. No. 11/846,068, on Feb. 21, 2012, 6 pages.
Office Action, issued by the United States Patent and Trademark Office in connection with U.S. Appl. No. 11/846,068, on Apr. 27, 2012, 9 pages.
Notice of Allowance and Fee(s) Due, issued by the United States Patent and Trademark Office in connection with U.S. Appl. No. 11/846,068, on Dec. 26, 2012, 9 pages.
Office Action, issued by the United States Patent and Trademark Office in connection with U.S. Appl. No. 12/835,714, onJan. 22, 2013, 34 pages.
Adamic et al., "The political blogosphere and the 2004 U.S. election: Divided they blog," Proceedings WWW-2005 2nd Annual Workshop on the Weblogging Ecosystem, 2005, Chiba, Japan, 16 pages.
Adar et al., "Implicit structure and the dynamics of blogspace," Proceedings WWW-2004 Workshop on the Weblogging Ecosystem, 2004, New York, NY, 8 pages.
Aliod et al., "A Real World Implementation of Answer Extraction," Department of Computer Science, University of Zurich, Winterthurerstr. 190, CH-8057 Zurich, Switzerland, 6 pages. Jan. 14, 2000.
Bishop, Mike, "ARROW Question/Answering Systems," Language Computer Corporation, 1999, 3 pages.
Bizrate, archived version of www.bizrate.com, Jan. 1999, 22 pages.
Blum, "Empirical Support for Winnow and Weighted-Majority Algorithms; Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses, and Digital Pseudonymns," Communication of the ACM, vol. 24, No. 2, 1981, 5 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, A1 Access Foundation and Morgan Kaufmann Publishers, USA, 1996, 17 pages.
Dagan et al., "Mistake-Driven Learning in Text Categorization," in EMNLP '97, $2^{nd}$ Conference on Empirical Methods in Natural Language Processing, 1997, 9 pages.
Delahaye Group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Dialogic, www.dialogic.com as archived on May 12, 2000, 34 pages.
Dillon et al., "Marketing research in a Marketing Environment," Times Mirror/Mosby College, USA, 1987, 5 pages.
Ewatch, eWatch's archived web site retrieved from [URL:http://web.archive.org/web/19980522190526/wwww.ewatch.com] on Sep. 8, 2004, archived May 22, 1998, 50 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Farber, Dave, "IP: eWatch and Cybersleuth," retrieved from [URL:http://www.interesting-people.org/archives/interesting-people/200006/msg00090.html] Jun. 29, 2000, 4 pages.
Freund et al., "Selective Sampling Using the Query by Committee Algorithm," Machine Learning 28 Kluwer Academic Publishers, The Netherlands, 1997, 36 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug 21-24, 2005, 10 pages.
Grefenstette et al., "Validating the Coverage of Lexical Resources for Affect Analysis and Automatically Classifying New Words along Semantic Axes," Chapter X, Mar. 3, 2004, 16 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Housley et al., "Internet X.509 Public Key Infrastructure Certificate and CRL Profile," Network Working Group Request for Comments: 2459, Jan. 1999, 121 pages.
Joachims, Thorsten, "Text Categorization with Support Vector Machines: Learning with Many Relevant Features," in Machine Learning: ECML-98, Tenth European Conference on Machine Learning, 1998, 7 pages.
Kahn et al., "Categorizing Web Documents using Competitive Learning: An ingrediant of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kleppner, "Advertising Procedure," 6th edition, 1977, Prentice-Hall, Inc., Englewood Cliffs, NJ, p. 492, 3 pages.
Kotler, "Marketing Management," PrenticeHall International Inc., Upper Saddle River, NJ, 1997, 10 pages.
Klimesch, "EEG alpha and theta oscillations reflect cognitive and memory performance: a review and analysis," Brain Research Reviews, vol. 29, 1999, 27 pages.
Lenz et al., "Question answering with Textual CBR," Department of Computer Science, Humboldt University Berlin, D-10099 Berlin, 1998, 12 pages.
Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.
Marlow, "Audience, structure and authority in the weblog community," International Communication Association Conference, MIT Media Laboratory, New Orleans, LA 2004, 9 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 301 pages.
Moldovan et al., "LASSO: A Tool for Surfing the Answer Net," Department of Computer Science and Engineering at Southern Methodist University, 1999, 9 pages.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
NetCurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Pang et al., "Thumbs up? Sentiment Classification using Machine Learning Techniques," in Proceedings of EMNLP 2002, 8 pages.
Reguly, "Caveat Emptor Rules on the Internet," The Globe and Mail (Canada): Report on Busiess Column, Apr. 10, 1999, 2 pages.
Reinartz, "Customer Lifetime Value Analysis: An Integrated Empirical Framework for Measurement and Explanation," dissertation: Apr. 1999, 68 pages.

(56) References Cited

OTHER PUBLICATIONS

Schmidt et al., "Frontal brain electrical activity (EEG) distinguishes valence and intensity of musical emotions," Cognition and Emotion, vol. 15 (4), Psychology Press Ltd, 2001, 14 pages.

Sammler, "Music and emotion: Electrophysiological correlates of the processing of pleasant and unpleasant music," Psychophysiology, vol. 44, Blackwell Publiching Inc., 2007, 12 pages.

Soderland et al., "Customer Satisfaction and Links to Customer Profitability: An Empirical Examination of the Association Between Attitudes and Behavior," SSE/EFI Working Paper Series in Business Administration, Jan. 1999, 22 pages.

Thomas, "International Marketing," International Textbook Company, Scranton, PA 1971, 3 pages.

Trigaux, Robert, "Cyberwar Erupts Over Free Speech Across Florida, Nation," Knight-Ridder Tribune Business News, May 29, 2000, 4 pages.

Tull et al, "Marketing Research Measurement and Method," MacMillan Publishing Company, New York, NY, 1984, 9 pages.

Voorhees, Ellen M., "The TREC-8 Question Answering Track Report," National Institute of Standards and Technology, 1999, 6 pages.

Wiebe et al., "Identifying Collocations for Recognizing Opinions," in proceedings of ACL/EACL '01 Workshop on Collocation, Toulouse, France, Apr. 9, 2001, 9 pages.

Word of Mouth Research Case Study, "The Trans Fat Issue, Analysis of online consumer conversation to understand how the Oreo lawsuit impacted word-of-mouth on trans fats," Aug. 16, 2004, 35 pages.

Yang, "An Evaluation of Statistical Approaches to Text Categorization," Information Retrieval 1 (1/2) Apr. 10, 1999, 12 pages.

Zagat, www.zagat.com, archived on Apr. 29, 1999, 33 pages.

Zagat, www.zagat.com, archived version of p. 34, Feb. 1999, 1 page.

Non Final Office Action, issued by the United States Patent and Trademark Office in connection with U.S. Appl. No. 11/500,678 on Mar. 18, 2014, 10 pages.

European Office Action, issued by the European Patent Office in connection with European Patent Application No. 07 838838.6 on Mar. 12, 2014, 3 pages.

Notification of Reasons(s) for Rejection, issued by the Japanese Intellectual Property Office in connection with Japanese Patent Application No. 2009-552660 Jan. 21, 2014, 4 pages.

\* cited by examiner

METHOD AND SYSTEM FOR RATING MEDIA AND EVENTS IN MEDIA BASED ON PHYSIOLOGICAL DATA

RELATED APPLICATIONS

This application claims priority to U.S. Provisional Patent Application No. 60/905,616, filed Mar. 8, 2007, and entitled "Method And System For Rating Media And Events In Media Based On Physiological Data," by Hans C. Lee, et. al., and is hereby incorporated herein by reference.

This application is related to and cross-references U.S. patent application Ser. No. 11/804,517, filed concurrently, and entitled "A Method And System For Using Coherence Of Biological Responses As A Measure Of Performance Of A Media," by Hans C. Lee, et. al., the contents of which application are hereby incorporated by reference.

BACKGROUND

1. Field of Invention

This invention relates to the field of media and event rating based on physiological response from viewers.

2. Background of the Invention

Prior approaches to analyze viewers' responses to a media focus around a top down view, which is based on an averaged response to a survey, viewer "knobs", physiological data or other rating schemes. This view limits the accuracy of the analysis due to cognitive bias of each individual viewer, as the viewer usually only remembers a small number of key events and forgets others. Consequently, one or two negative events in the media can dominate what the viewer thinks of the media afterwards, even if other positive events happened during the viewer's experience of the media.

The physiological data, which includes but is not limited to heart rate, brain waves, motion, muscle movement, galvanic skin response, and others responses of the viewer of the media, can give a trace of the viewer's emotion changes while he/she is watching the media. However, such data by itself does not create an objective measure of the media that allows the media or its events to be benchmarked and/or compared to other instances of media or events objectively.

SUMMARY OF INVENTION

Various embodiments of the present invention enable a bottom up analysis approach that derives physiological responses from measured physiological data of viewers of a media, and calculates scores of instances of an event type based on the physiological responses. The scores are then aggregated to rate the event type in addition to scoring the individual event instances. The approach can further form an overall rating of the media by aggregating the ratings of set of event types within the media.

DETAILED DESCRIPTION OF EMBODIMENTS OF THE INVENTION

The invention is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

An effective media that connects with its audience/viewers is able to elicit the desired emotional response and it is well established that physiological response is a valid measurement for viewers' changes in emotions. Various embodiments of the present invention enable a bottom up analysis approach that derives physiological responses from measured physiological data of viewers of a media, and calculates scores of instances of an event type based on the physiological responses. The scores are then aggregated to rate the event type in addition to scoring the individual event instances. The approach can further form an overall rating of the media by aggregating the ratings of set of event types within the media. Such an approach allows instances of an event type to be objectively measured against prior instances of the same event type in the media, and the current media to be objectively measured against another media. In addition, a slice and combine approach can be adopted, which defines the media into one or more key and repeatable event types each having a plurality of event instances based on the physiological data measured, and then aggregates the score of every event instance and every event type to measure the viewers' overall responses to the media. The entire approach can also be automated as each step of the approach can be processed by a computing device, allowing for objective measure of a media without much human input or intervention.

A key principle behind the present invention is that one cannot look at an individual response to a media and make a judgment about the media. For a non-limiting example, a movie having multiple key scenes (events) can only be ranked accurately via a full analysis of viewers' responses to each of the scenes. Such analysis includes but is not limited to whether the intense scenes were actually intense, whether the love scenes turn viewers off or engage them, whether the viewers thought the jokes were funny, etc. Only when these individual scene types are aggregated and evaluate as a whole, can the movie be compared objectively and automatically to other movies in the same genre. In addition, only by knowing the typical response to be expected to a certain scene (event type), can a new instance of the scene be rated objectively.

Figure 1:
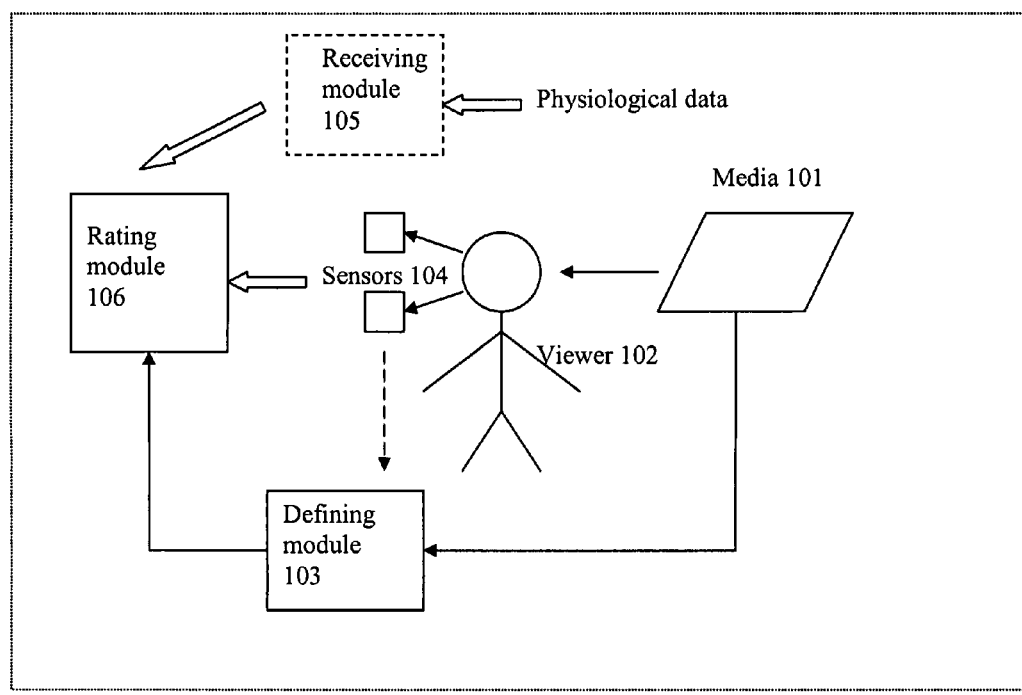
FIG. 1 is an illustration of an exemplary system to support media and events rating in accordance with one embodiment of the present invention.

FIG. 1 is an illustration of an exemplary system to support media and events rating in accordance with one embodiment of the present invention. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 1, one or more sensors 104 are utilized to measure and record physiological data from each of a plurality of viewers 102 who are watching a media 101. Alternatively, an integrated sensor headset can be adopted as discussed in details later. Here, the media can be one or more of a movie, a video, a television program, a television commercial, an advertisement, a video game, an interactive online media, a print, and any other media from which a viewer can learn information or be emotionally impacted. The physiological data measured can include but is not limited to, heart rate, brain waves, electroencephalogram (EEG) signals, blink rate, breathing, motion, muscle movement, galvanic skin response and any other response correlated with changes in emotion. Each of the one or more sensors can be one of: an electroencephalogram, an accelerometer, a blood oxygen sensor, a galvanometer, an electromyograph, and any other physiological sensor. Physiological data in the body have been shown to correlate with emotional changes in humans. By sensing these exact changes instead of using surveys, knobs or other easily biased measures of response, the present invention improves both the data that is recorded and the granularity of such data as physiological responses can be recorded many times per second.

In some embodiments, a receiving module 105 is operable to accept and/or record the physiological data of each of a plurality of viewers watching the media, wherein the physiological data may be measured and/retrieved via other means and/or from a storage.

In some embodiments, a defining module 103 is operable to define and mark occurrences and durations of one or more event types each having a plurality of event instances happening in the media. The duration of each of event instances in the media can be constant, non-linear, or semi-linear in time. In some embodiments, such event definition may happen after the physiological data of the viewers has been measured, where the defining module 103 can define the media into one or more event types each having a plurality of event instances in the media based on the physiological data measured from the plurality of viewers.

In some embodiments, a rating module 106 is operable to derive a plurality of physiological responses from the physiological data measured from the plurality of viewers and calculate a score for each of the plurality of event instances of one of the event types in the media based on the plurality of physiological responses. Here, the physiological response can be one or more of: thought, liking, engagement, immersion, physical engagement, valence, and vigor, wherein thought and liking can be calculated from EEG. The rating module is further operable to rate the specific event type by aggregating the scores of instances of the event type once such scores are calculated. In addition, the rating module may optionally rate the media by aggregating ratings of the event types in the media.

Figure 2:
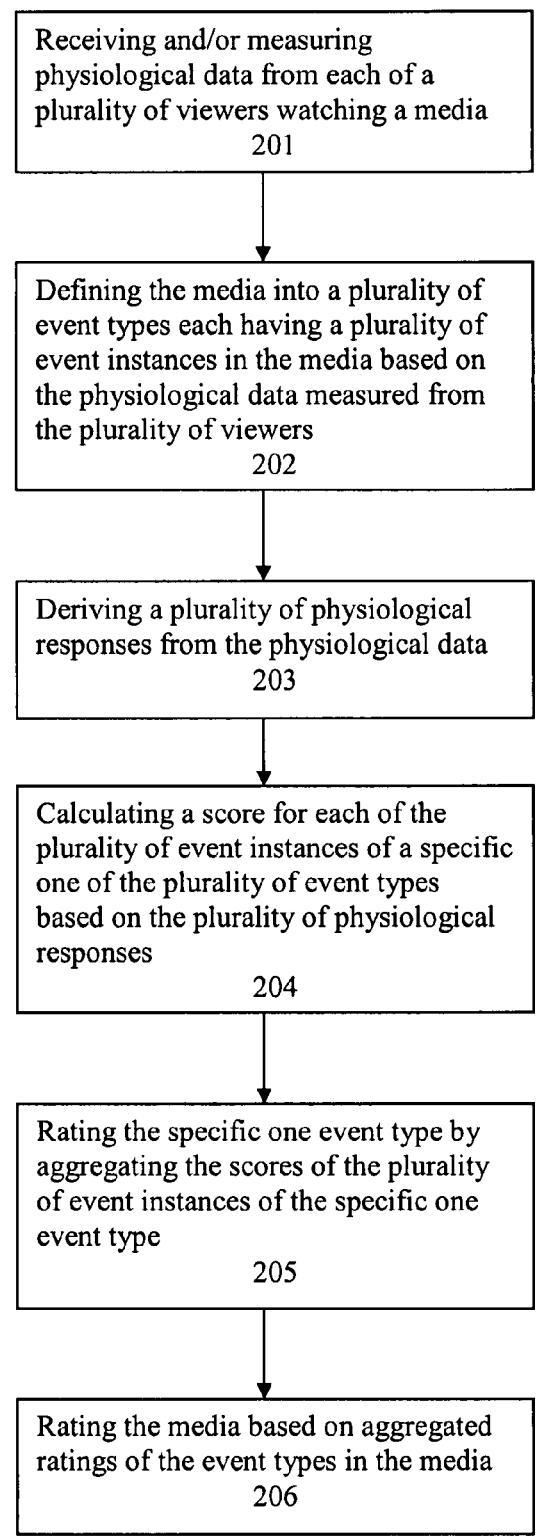
FIG. 2 (a)-(b) are flow charts illustrating exemplary processes to support media and events rating in accordance with one embodiment of the present invention.
Figure 2:
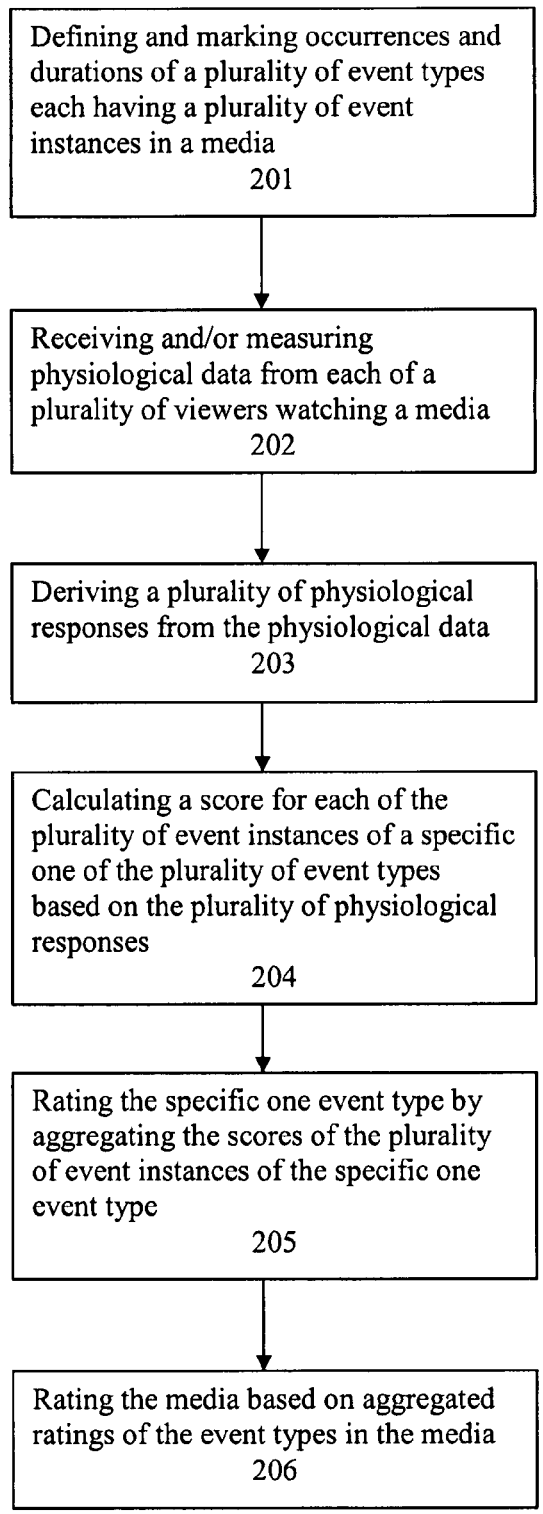

FIG. 2 (a)-(b) are flow charts illustrating exemplary processes to support media and events rating in accordance with one embodiment of the present invention. Although this figure depicts functional steps in a particular order for purposes of illustration, the process is not limited to any particular order or arrangement of steps. One skilled in the art will appreciate that the various steps portrayed in this figure could be omitted, rearranged, combined and/or adapted in various ways.

Referring to FIG. 2 (a), physiological data from each of a plurality of viewers watching a media is received or measured at step 201. The media can then be defined into a plurality of event types each having a plurality of event instances in the media based on the physiological data measured from the plurality of viewers at step 202. A plurality of physiological responses can be derived from the physiological data at step 203. At step 204, a score for each of the plurality of event instances of a specific event type is calculated based on the plurality of physiological responses, and step 205 rates the specific event type by aggregating the scores of the plurality of event instances of the specific event type. Step 204 and 205 can be repeated for each type in the media, and the media itself can be rated based on aggregated ratings of the event types in the media at step 206.

In some embodiments, the physiological data can be used to define the media into key, repeated event instances/types that are comparable across other media in the same genre. Referring to FIG. 2 (b), occurrences and durations of a plurality of event types each having a plurality of event instances in a media can be defined and/or marked at step 201, before physiological data from each of a plurality of viewers watching the media is received or measured at step 202. Step 203-206 are identical to those steps shown in FIG. 2(a).

Figure 3:
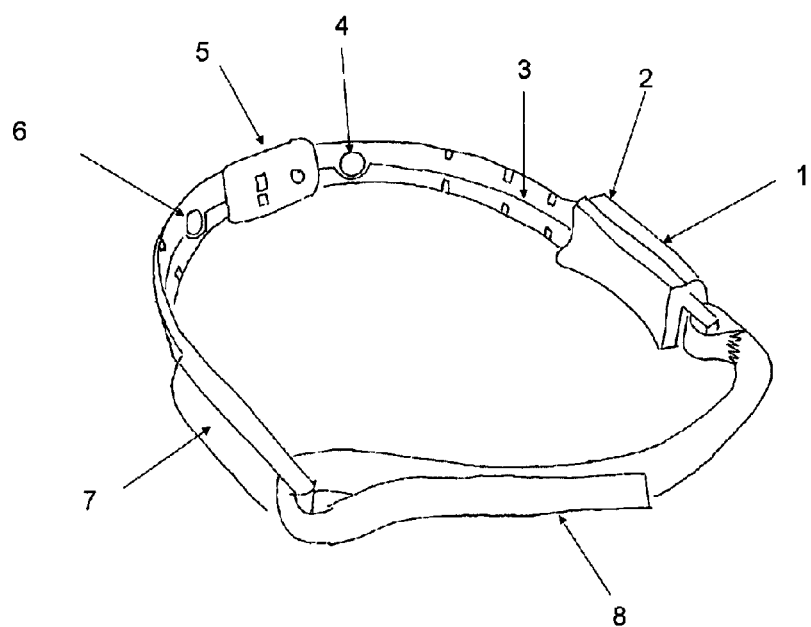
FIG. 3 shows an exemplary integrated headset used with one embodiment of the present invention.

In some embodiments, an integrated physiological sensing headset capable of sensing a plurality of measures of biological response can be placed on a viewer's head for measurement of his/her physiological data while the viewer is watching an event of the media. The data can be recorded in a program on a computer that allows viewers to interact with media while wearing the headset. FIG. 3 shows an exemplary integrated headset used with one embodiment of the present invention. Processing unit 301 is a microprocessor that digitizes physiological data and then processes it into physiological responses that include but are not limited to thought, engagement, immersion, physical engagement, valence, vigor and others. A three axis accelerometer 302 senses movement of the head. A silicon stabilization strip 303 allows for more robust sensing through stabilization of the headset that minimizes movement. The right EEG electrode 304 and left EEG electrode 306 are prefrontal dry electrodes that do not need preparation to be used. Contact is needed between the electrodes and skin but without excessive pressure. The heart rate sensor 305 is a robust blood volume pulse sensor positioned about the center of the forehead and a rechargeable or replaceable battery module 307 is located over one of the ears. The adjustable strap 308 in the rear is used to adjust the headset to a comfortable tension setting for many different head sizes.

In some embodiments, the integrated headset can be turned on with a push button and the viewer's physiological data is measured and recorded instantly. The data transmission can be handled wirelessly through a computer interface that the headset links to. No skin preparation or gels are needed on the viewer to obtain an accurate measurement, and the headset can be removed from the viewer easily and can be instantly used by another viewer, allows measurement to be done on many participants in a short amount of time and at low cost. No degradation of the headset occurs during use and the headset can be reused thousands of times.

Figure 4:
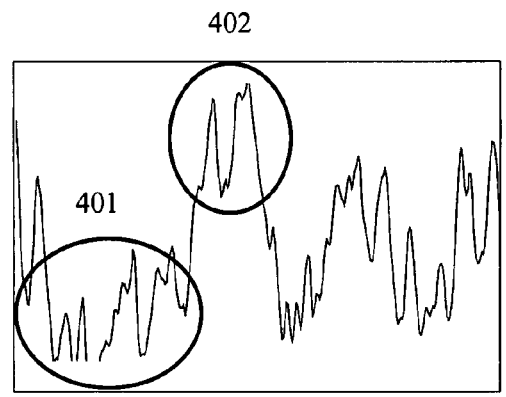
FIG. 4(a)-(c) show exemplary traces of physiological responses measured and exemplary dividing lines of a media in accordance with one embodiment of the present invention.
Figure 4:
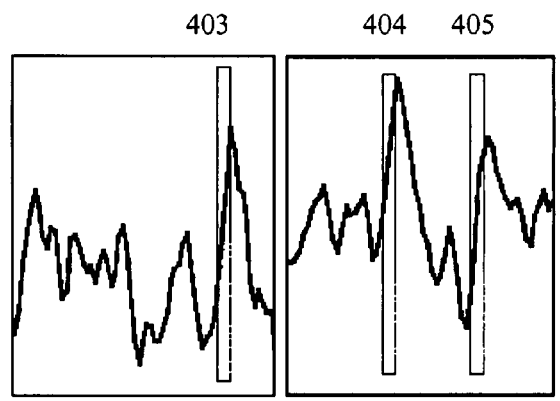
Figure 4:
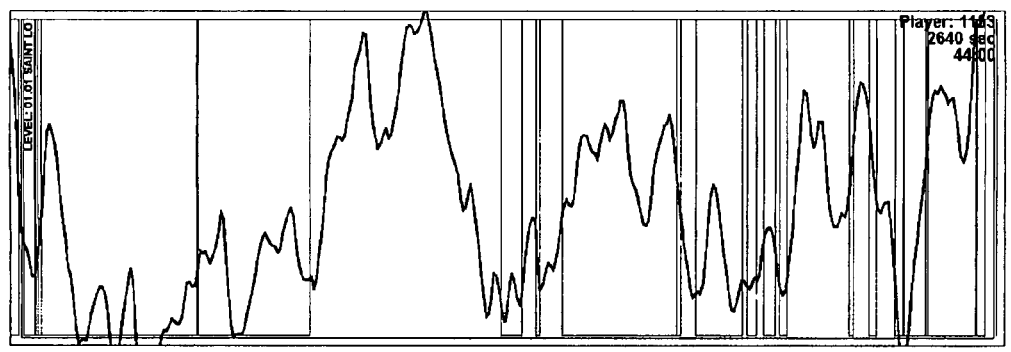

In some embodiments, the viewers' physiological responses can be derived via a plurality of formulas, which use the physiological data of the viewers as inputs. Facial expression recognition, "knob" and other measures of emotion can also be used as inputs with comparable validity. Each of the derived physiological responses, which can include but are not limited to, "Engagement," "Adrenaline," "Thought,"

and "Valence," combines physiological data from multiple sensors into a multi-dimensional, simple-to-understand, representation of viewers' emotional response. FIG. 4(a) shows an exemplary trace of "Engagement" for a player playing Call of Duty 3 on the Xbox 360 measured in accordance with one embodiment of the present invention. The trace is a time based graph, with the beginning of the session on the left and the end on the right. Two sections (event instances) 401 and 402 are circled, where 401 on the left shows low "Engagement" during a game play that happens during a boring tutorial section. 402 shows a high "Engagement" section that has been recorded when the player experiences the first battle of the game.

In some embodiments, the viewers' physiological responses (e.g., strong, boring, funny, engaging, etc) over a large number of instances of each event type can be calculated, analyzed and correlated with the measures of such responses to individual event types (e.g., branding moment, product introduction, video game cut scene, fight, level restart, etc) to create a context-specific event profile for each event type. These profiles can then be used to rate each event instance that happens in a new piece of media, creating, in some cases, thousands to millions of individual bottom up measures of the media over up to hundreds to thousands of participating viewers. Combining this many individual scores greatly increases the accuracy of measurement of the overall media compared to asking survey questions and getting one hundred responses to 1 to 10 dimensions of subjective measures. For a non-limiting example of 100 viewers watching a movie having 1000 key event instances, 5 dimensions of physiological responses (e.g., thought, engagement, valence, immersion, physical engagement) are calculated for each of the viewers, and 6 math permutations (e.g., average value, deviation from mean, 1st order trend, 2nd order trend, positive response, negative response, etc) are calculated for each event instance based on the physiological responses of the viewers. Consequently, 3,000,000 (100*1000*5*6) pieces of scores are available to rate the movie vs. 100-1000 measures from surveys. These scores are then combined to create an overall rating for the movie, such rating may include but is not limited to, Individual event (scene) strength—did players like cut scenes, were jokes funny, overall quality of the events, strong and weak types of events, strong and weak events of the movie—the events in the middle had a strong response but the beginning ones did not.

In some embodiments, the occurrence and duration of an event instance or type can be defined and recorded. For a non-limiting example, an event type in a video game may be defined as occurring every time a "battle tank" appears in the player's screen and lasting as long as it remains on the screen. For another non-limiting example, an event in a movie may be defined as occurring every time a joke is made. An event type may be defined in such a way that an instance of the event type occurs only once for each piece of media. Alternatively, the event type may also be defined in such a way that many instances of the event type occur in a media.

In some embodiments, event instances can be tagged for each recorded piece of media, allowing for efficient and accurate conclusions to be made. For a non-limiting example, FIG. 4(b) shows two exemplary traces of the "Engagement" data of a video game player measured in accordance with one embodiment of the present invention. The boxes 403, 404, and 405 in the pictures correspond to a specific "weapon use" event type that has been tagged. At each point where the event instance appears, "Engagement" rises sharply. The picture in FIG. 4(b) shows one type of event being tagged, but the approach can be extended to many event instances being tagged with different event types, allowing the media to be sliced into pieces. For another non-limiting example, FIG. 4(c) shows exemplary vertical lines that divide the piece of media into event instances in accordance with one embodiment of the present invention. Key event types define every important thing that a player of the video game or other media may encounter and/or interact with. Here, the physiological data/response is overlaid with the tags of the event instances, and both can be toggled on and off.

In some embodiments, a score can be generated for an event instance based on the physiological data or response of the viewer during the event instance using a formula or rule. In one embodiment, the formula can be based on expert knowledge of the desired response to the event type of the instance and the formula can take the form of a weighted sum of the changes in each of the derived physiological responses across the event instance. For a non-limiting example, the formula can be defined by a weighted sum of multiple inputs from each of physiological responses over time (vector), wherein each of the vectors may rise, fall, peak, reach high, reach low, or have a distinct profile. For a non-limiting example, there can be a profile of the physiological response to punch lines in jokes that correlates with how good the joke is based on the analysis of many advertisements. There can be two aspects of the profile: the first is that the "Thought" vector of physiological response must increase, showing that the viewer thought about what was happening directly before the punch line and during the first part of the punch line; the second is that the "Valence" or reward feeling for viewers must increase once the punch line is given, indicating that the viewers liked the punch line after engaging in thinking about the punch line. Thus, a mathematical profile of rise in Thought and Valence at specific times is created for the event type of a joke. Such profile can then be applied to each instance of a joke to assess the effectiveness of the punch line of the joke. Punch lines that do not fit this response profile will not create a good experience in viewers.

Figure 5:
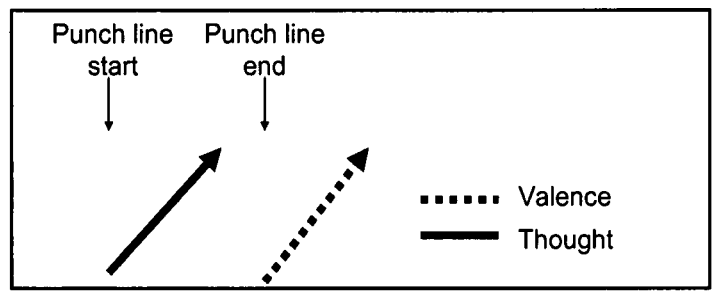
FIG. 5 shows an exemplary profile of a joke in an advertisement as generated in accordance with one embodiment of the present invention.

FIG. 5 shows an exemplary profile of Joke Punchlines in an advertisement as generated in accordance with one embodiment of the present invention. The profile can be created either through expert knowledge of the subject matter or through a mathematical formula. If the physiological response of an instance of this event type matches this profile, the event instance is considered a success. For a non-limiting example, the following formula can be used to calculate the score of an instance of the joke:

$$\text{Score}=0.25\times(\text{Thought Rose during punch line})+0.75\times(\text{Valence rose after punch line})$$

Where the resulting weights are 25% based on Thought rising during the punch line and 75% based on Valence rising after the punch line.

In some embodiments, scores of event instances in the media can be used to pinpoint whether and/or which of the event instances need to be improved or changed, and which of the event instances should be kept intact based on the physiological responses from the viewers. In the non-limiting example above, a punch line that does not fit its response profile and thus does not create a good experience in viewers should be improved.

In some embodiments, the number of variables used in the scoring formula can be very large and the formula can also be a higher ordered polynomial to account for non-linear scoring if need be. For a non-limiting example, a more complex version of the formula shown above would calculate the score based on how much thought and how much positive valence there is at each point during the joke. This would penalize small increases in Thought and Valence where people did not strongly engage in the joke, while rewarding punch lines which had very large rises in Thought and Valence, corresponding to strong engagement in the joke.

In some embodiments, a set of logical rules can be adopted, which define an event instance as "good" or "successful" as having a score above a predetermined number, whereby the formula outputs a score reflecting how engaging the event instance is. Other embodiments use the score for rankings or ratings are also possible. Referring back to the non-limiting example shown in FIG. 4(b) where a weapon event type is tagged, the simple explanation of the profile for this event type is that if Engagement rises strongly, an event instance of the type is good. In this example, all event instances are good, which would lead to a high score for the event type. This calculation scheme can be done over hundreds of instances of multiple key event types.

In some embodiments, the formula can utilize prior instances of similar event types in the current and/or other pieces of media to calculate the score of the instance. A set of rules can be created with viewers' physiological responses across those other similar events as inputs. For a non-limiting example, a score of 1 (representing "good" or "successful") could be given to an instance of an event type if the slope of Engagement over the event exceeds the average slope of Engagement over other event instances of similar event types in other pieces of media. The exact implementation of this approach can be done many ways, and the following process is a non-limiting example of such implementation:

1. Tagging a large set of instances of an event type in the media along with the physiological responses from the viewers of these instances.
2. Choosing a rating mechanism to allow for each instance of the event type to be rated.
3. Calculating various different mathematical measures of the physiological responses from the viewers over an event instance. Such measures may include but are not limited to, average, 1st order derivative, 2nd order derivative, polynomial approximations, (standard) deviations from the mean, (standard) deviations of derivatives from the mean, and profiles of the physiological responses, which can be implemented with convolution or other methods that takes into account one or more of: peaking in the middle, spiking in the beginning, being flat, etc.
4. Repeating calculation at step 3 for all physiological responses.
5. Transforming the large number of measures into defined outcome (score) for the event instance. Such transformation can be done via one or more of: convolution, weighted sum, positive or negative slope, a polynomial formula, least squares, support vector machines, neural networks and other machine learning approaches.
6. Repeating transformation at step 5 for all instances of the event type. A ranking, rating or score for each individual event instance can be calculated via this or any other similar approaches, allowing instances of an event type to be compared objectively.

In some embodiments, a subset of the overall population of viewers can be aggregated to differentiate the responses for the subset, which groups the viewers by one or more of: race, gender, age, buying habits, demographics, and income. The averaged rating of the event type can then be associated and/or compared to such grouping of the viewers.

In some embodiments, the scores of event instances of an event type can be aggregated as input to a formula used to rate of the event type, where the formula may be mathematical or may be logical; it may also be designed by expert knowledge or by previous ratings of similar event types. Such aggregation can be done via one or more of:

Averaging for each event type. This approach averages the scores of all event instances of the event type throughout the media and also over many viewers.

Performance. A simple average may not always give an accurate view of the overall performance of the media. For a non-limiting example, if 75% of event instances are very highly rated, while the rest are mediocre, the overall rating of the event type may be around 75-80%, which could seem to be good. In reality however, the viewers who watch the media will not like one quarter of the media, which leads to a very low score. A performance metric takes into account the distribution of scores of instances of the event type. Using prior distributions of the instances as a reference, the performance metric can define how good the overall distribution of the instances is and if viewers will like the event type/media or not. One non-limiting implementation of performance metric can be done through histogram matching for the event type.

"Success" ratio. The formulas output a "success" ratio in percentage points, or another score for each event type. More specifically, a "success" ratio of an event type can be defined via an aggregated view of the performance of the event type/media in a specific aspect characterized by the definition of the event type, and a "success" ratio above a predetermined number is defined to be a successful event type.

Figure 6:
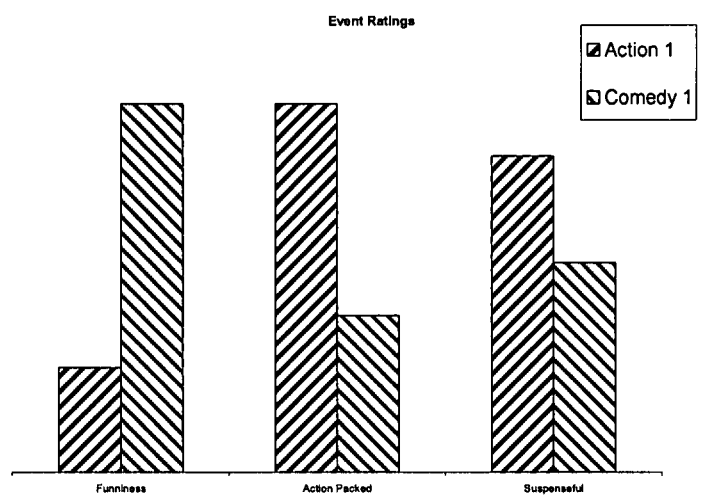
FIG. 6 shows overall event ratings for three exemplary types of events in two movies calculated in accordance with one embodiment of the present invention.

In some embodiments, the rating process described above can be repeated for different types of events within the same media. In addition, the media itself can be rated with the ratings of different event types used as inputs to a rating formula. This rating formula or rule can also be based on expert knowledge or previous physiological response to the media as described above. For a non-limiting example, a media can be rated as "success" if a majority of its event types are rated as "success." Alternatively, a media can be rated as "success" its event types are rated as "success" more than other comparable media. Other rules, linear or other rating scales can also be used. FIG. 6 shows overall event ratings for three exemplary types of events in two movies calculated in accordance with one embodiment of the present invention. The first movie is an action movie and the response to the "Action Packed" and "Suspenseful" event types is very strong while the "Funniness" event type, such as jokes do not create a strong response. The second movie is a comedy, which creates the opposite responses compared to the action movie. Both movies are given a high rating because the event types have the correct profile for a successful movie in their genre.

One embodiment may be implemented using a conventional general purpose or a specialized digital computer or microprocessor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention may also be implemented by the preparation of integrated circuits or by interconnecting an appropriate network of conventional component circuits, as will be readily apparent to those skilled in the art.

One embodiment includes a computer program product which is a machine readable medium (media) having instructions stored thereon/in which can be used to program one or more computing devices to perform any of the features presented herein. The machine readable medium can include, but is not limited to, one or more types of disks including floppy disks, optical discs, DVD, CD-ROMs, micro drive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data. Stored on any one of the computer readable medium (media), the present invention includes software for controlling both the hardware of the general purpose/specialized computer or microprocessor, and for enabling the computer or microprocessor to interact with a human viewer or other mechanism utilizing the results of the present invention. Such software may include, but is not limited to, device drivers, operating systems, execution environments/containers, and applications.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Particularly, while the concept "module" is used in the embodiments of the systems and methods described above, it will be evident that such concept can be interchangeably used with equivalent concepts such as, class, method, type, interface, bean, component, object model, and other suitable concepts. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A method comprising:
analyzing physiological data from a plurality of viewers exposed to media to define a plurality of events in the media and to derive a plurality of physiological response dimensions from the physiological data for the plurality events;
calculating a first score for a first event using at least two of the plurality of physiological response dimensions, the first score calculated by weighting a first physiological response dimension with a first weight;
calculating a second score for a second event using at least two of the plurality of physiological response dimensions, the second score calculated by weighting a second physiological response dimension with a second weight, different than the first weight, a value of the first weight and a value of the second weight being determined based on the type of event; and
creating a rating for the media based on an aggregate of the plurality of scores for the plurality of events.

2. A method comprising:
analyzing physiological data from a plurality of viewers exposed to media to define a plurality of events in the media and to derive a plurality of physiological response dimensions from the physiological data for the plurality events;
calculating a first score for a first event using at least two of the plurality of physiological response dimensions, the first score calculated by weighting a first physiological response dimension with a first weight;
calculating a second score for a second event using at least two of the plurality of physiological response dimensions, the second score calculated by weighting a second physiological response dimension with a second weight, different than the first weight, a value of the first weight and a value of the second weight being determined based on the type of physiological response dimension, a valence physiological response dimension being weighted more than a thought physiological response dimension; and
creating a rating for the media based on an aggregate of the plurality of scores for the plurality of events.

3. A method comprising:
analyzing physiological data from a plurality of viewers exposed to media to define a plurality of events in the media and to derive a plurality of physiological response dimensions from the physiological data for the plurality events;
calculating a first score for a first event using at least two of the plurality of physiological response dimensions;
calculating a second score for a second event using at least two of the plurality of physiological response dimensions;
calculating a plurality of additional scores, wherein the total number of scores calculated for the media equals the product of (1) a total number of viewers, (2) a total number of events defined by the processor, (3) a total number of physiological dimensions used by the processor, and (4) a total number of mathematical operations used by the processor; and
creating a rating for the media based on an aggregate of the plurality of scores for the plurality of events.

* * * * *